US00RE39888E

(19) United States
(12) Reissued Patent
Llagostera et al.

(10) Patent Number: US RE39,888 E
(45) Date of Reissued Patent: Oct. 16, 2007

(54) PROCESS FOR OBTAINING QUINAPRYL HYDROCHLORIDE AND SOLVATES USEFUL FOR ISOLATING AND PURIFYING QUINAPRYL HYDROCHLORIDE

(75) Inventors: Montserrant Monsalvatje Llagostera, Barcelona (ES); Marti Bartra Sanmarti, Barcelona (ES); Jaime Thomas Navarro, Barcelona (ES); Salvador Puig Torres, Barcelona (ES)

(73) Assignee: Esteve Quimica, S.A., Barcelona (ES)

(21) Appl. No.: 11/022,424

(22) PCT Filed: May 25, 1998

(86) PCT No.: PCT/ES98/00145

§ 371 (c)(1),
(2), (4) Date: Jun. 17, 2002

(87) PCT Pub. No.: WO98/54149

PCT Pub. Date: Dec. 3, 1998

(Under 37 CFR 1.47)

Related U.S. Patent Documents

Reissue of:
(64) Patent No.: 6,617,457
Issued: Sep. 9, 2003
Appl. No.: 09/424,673
Filed: Jun. 17, 2002

(30) Foreign Application Priority Data

May 29, 1997 (ES) ..... 9701169

(51) Int. Cl.
*C07D 217/26* (2006.01)

(52) U.S. Cl. ..... 546/147
(58) Field of Classification Search ..... 546/147
See application file for complete search history.

(56) References Cited

U.S. PATENT DOCUMENTS 4,344,949 A * 8/1982 Hoefle et al. ..... 514/307
4,761,479 A * 8/1988 Goel et al. ..... 546/147

FOREIGN PATENT DOCUMENTS

BE 892552 * 9/1982

* cited by examiner

*Primary Examiner*—Zinna N. Davis
(74) *Attorney, Agent, or Firm*—Morgan & Finnegan, L.L.P.

(57) ABSTRACT

The process for obtaining quinapril hydrochloride (I) comprises the stages of: a) hydrogenolysis of the benzyl ester of quinapril (II) by treatment in an alcoholic solvent, with concentrated hydrochloric acid or a solution of hydrogen chloride in isopropanol, and hydrogenation; b) removal of the solvent; c) addition of toluene to precipitate the quinapril hydrochloride as a toluene solvate; d) treatment of said solvate with a Class 3 solvent which forms a solvate of quinapril hydrochloride from which it can be removed by drying without degrading; and e) drying of the solvate from step d) to yield quinapril hydrochloride (I), an antihypertensive agent.

(I)

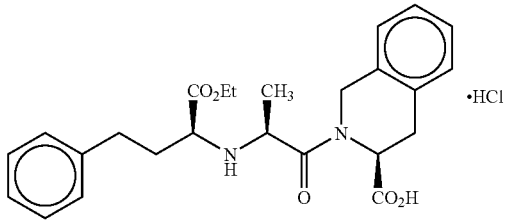

(II)

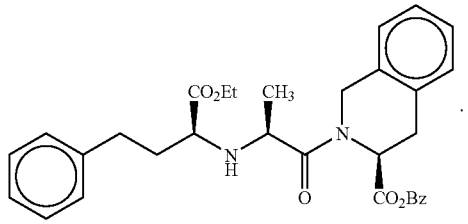

29 Claims, No Drawings

PROCESS FOR OBTAINING QUINAPRYL HYDROCHLORIDE AND SOLVATES USEFUL FOR ISOLATING AND PURIFYING QUINAPRYL HYDROCHLORIDE

Matter enclosed in heavy brackets [ ] appears in the original patent but forms no part of this reissue specification; matter printed in italics indicates the additions made by reissue.

This application is a 371 of PCT/ES98/00145 filed May 25, 1998.

FIELD OF THE INVENTION

This invention refers to a procedure for obtaining quinapril hydrochloride, as well as new solvates of quinapril hydrochloride, obtained by the use of Class 3 solvents, from which it is possible to eliminate the solvent by drying without degradation of the product, and which are useful for the isolation and purification of quinapril hydrochloride. The process can be developed at the industrial scale.

BACKGROUND OF THE INVENTION

Quinapril is the common international denomination of the chemical compound named (S)-2-[(S)—N—[(S)-1-(ethoxycarbonyl-3-phenylpropyl]-L-alanyl]-1,2,3,4-tetrahydro-3-isoquinolinecarboxylic acid]. Quinapril and its pharmaceutically acceptable salts are antihypertensive agents which act as angiotensin converting enzyme (ACE) inhibitors.

The first description of quinapril appears in the U.S. Pat. No. 4,344,949, which also describes its preparation starting from the ethyl ester of (S,S)-α-[(1-carboxyethyl)amino] phenylbutanoic acid and from the benzyl or t-butyl ester of (S)-1,2,3,4-tetrahydro-3-isoquinolinecarboxylic acid by peptide condensation with dicyclohexyl-carboimide (DCC) and activation with hydroxibenzotriazole. The benzyl or t-butyl ester of quinapril so obtained is unprotected by catalytic hydrogenation or by treatment with trifluoroacetic acid, being the final isolation of quinapril carried out (at the laboratory scale by preception with ethyl either and by lyophilization of an aqueous solution. The isolation of quinapril is a very delicate procedure, as this product degrades very easily by intramolecular cyclisation to yield a diketopiperazine of formula

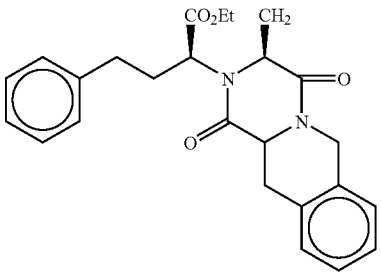

both in aqueous or organic solution as in the solid state.

The process described in said patent U.S. Pat. No. 4,344,949 presents the drawbacks which are typical of the use of DCC, as the condensations carried out in the presence of DCC yield a fair amount of impurities, with the subsequent reduction in the yield (61%), thus the resulting dicylohexylurea must be separated and, additionally, the carbodiimides are responsible for very severe allergies.

Quinapril hydrochloride is the salt which is usually employed in the manufacture medicinal products which contain quinapril.

The U.S. Pat. No. 4,761,479 mentions that obtaining and purifying quinapril hydrochloride is hindered by its ease in degrading into by-products, essentially the diketopiperazine shown before. Said U.S. Pat. No. 4,761,479 describes a process for obtaining quinapril hydrochloride which comprises unprotecting the t-butyl ester of quinapril with HCl gas in acetic acid, the isolation of the precipitation product after the addition of xylene and vacuum distillation, and the purification of the quinapril hydrochloride by crystallisation with acetonitrile to yield a crystalline solvate of acetonitrile. The solvent of said solvate can be removed, without degradation of the quinapril hydrochloride, by drying in a vacuum oven. However, acetonitrile is a Class 2 solvent, defined by the ICH [International Conference on Harmonisation of Technical Requirements for the Registration of Pharmaceuticals for Human Use] as a "Non-mutagenic carcinogen in animals or possible cause of other irreversible toxicity such as neurotoxicity, teratogenesis or suspect of significant reversible toxicity, and, therefore, its proportion has to be limited". In the case of acetonitrile, the ICH recommends a limit not above 250 ppm (0.025%). This limit is difficult to achieve at the industrial scale due to the little stability of the product.

The Belgian Patent No. BE 892.552 describes another process for the preparation of quinapril hydrochloride starting from (S,S)-α-[(1-carboxyethyl)amino]phenylbutanoic acid by activation with 1,1'-carbonyldiimidazole, which yields an N-carboxyanhydride which reacts in situ, without prior isolation, with the benzyl ester of (S)-1,2,3,4-tetrahydro-3-isoquinolinecarboxylic acid to yield the corresponding benzyl ester of quinapril with a yield of 56%. The resulting quinapril, protected in the form of a benzyl ester, is subsequently hydrogenated in the presence of Pd/C and it is treated with hydrochloric acid to give the quinapril hydrochloride, which is purified by chromatography and lyophilization, at a very low yield (37%). This synthetic route is also mentioned in a generic manner in the Spanish Patent ES 2.004.804, but without giving any specific conditions, nor yields, nor a description of the properties of the products obtained. Specifically, the synthesis of quinapril hydrochloride is not exemplified at all.

In general, all the processes described for obtaining quinapril hydrochloride are characterised by their difficulty or by their low yields. Only the U.S. Pat. No. 4,761,479 describes a process for the industrial isolation and purification of quinapril hydrochloride, starting from the t-butyl ester of quinapril. However, said procedure has the disadvantage of using a carcinogenic solvent (acetonitrile) to obtain the corresponding solvate.

Consequently, there is a need to have a process for obtaining and purifying quinapril hydrochloride, which may be carried out at the industrial scale, and which overcomes the previously mentioned drawbacks. In order to obtain and purify quinapril hydrochloride at a high yield, the invention proposes the precipitation of said product in the form of a toluene solvate. Therefore, one of the objects of the inventon is constituted by a process for obtaining quinapril hydrochloride, which comprises its isolation as the toluene solvate.

On the other hand, the solvates of quinapril hydrochloride, which are useful compounds for the purification of said product, are, in general, products from which it is extremely difficult to remove the solvent without partially degrading the quinapril hydrochloride. The only known solvate of quinapril hydrochloride which can be dried without degradation of the product is the acetonitrile solvate, but said solvate has been obtained with a carcinogenic solvent. In order to overcome these drawbacks, the invention provides solvates of quinapril hydrochloride which can be dried to remove the solvent without degrading the quinapril hydrochloride, and which have been obtained by the use of non-carcinogenic solvents. Therefore, an additional object of the invention is constituted by new solvates of quinapril hydrochloride, of solvents belonging to Class 3, from which it is possible to remove the solvent by drying without degradation of quinapril hydrochloride. Class 3 solvents are defined, according to the ICH, as "Solvents with a low toxic potential to man, not being it necessary to establish an exposure limit based on health criteria. Class 3 solvents have a ADE (Allowable Daily Exposure) equal or greater than 50 mg per day".

DETAILED DESCRIPTION OF THE INVENTION

The invention provides a process for obtaining quinapril hydrochloride of formula (I)

(I)

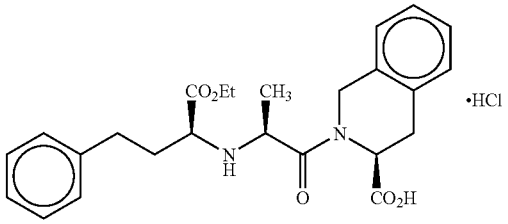

which comprises the stages of:

a) hydrogenolysis of the benzyl ester of quinapril (II)

(II)

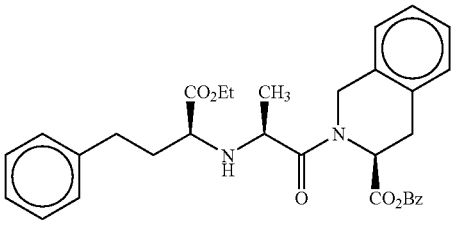

where Bz is the benzyl radical;

b) removal of the solvent used in step a);

c) addition of toluene to precipitate the quinapril hydrochloride as a toluene solvate;

d) treatment of the toluene solvate of quinapril hydrochloride with a solvent belonging to Class 3, capable of forming a solvate of quinapril hydrochloride from which it is possible to eliminate said solvent by drying in an oven without degrading the quinapril hydrochloride; and e) drying of the solvate obtained in step d) to yield quinapril hydrochloride (I).

The benzyl ester of quinapril (II) is a known product which can be obtained by whichever of the processes described in the patents U.S. Pat. No. 4,344,949 and BE 892,552, mentioned earlier, as well as in the patents EP 135181 and EP 135182 where it is described, in a general manner, the obtaining of the protected quinapril in the form of the benzyl ester starting from (S,S)-α-[(1-carboxyethyl) amino]phenylbutanoic acid, by activation with alkenephosohonic anhydrides.

The hydrogenolysis of the benzyl ester of quinapril (II) can be carried out in an alcoholic solvent, such as ethanol or isopropanol, with concentrated hydrochloric acid or with a solution of hydrogen chloride in isopropanol, hydrogenation with hydrogen gas at a pressure comprised between approximately $10^4$ Pa (0,1 bar) and approximately $2\times10^5$ Pa (2 bar) , at a temperature comprised between 10 and 40° C., in the presence of a suitable hydrogenation catalyst, for instance, Pd/C.

In a specific embodiment, the hydrogenolysis reaction is carried out using ethanol as a solvent, concentrated hydrochloric acid, a pressure of $10^5$ Pa (1 bar) and room temperature. In another specific embodiment, the hydrogenolysis reaction is carried out using isopropanol as a solvent, a solution of hydrogen chloride in isopropanol, a pressure of $2\times10^5$ Pa (2 bar) and a temperature of approximately 30° C.

The molar ratio between the benzyl ester of quinapril (II) and hydrochloric acid can be equal or slightly greater to the stoichiometric one, although preferably said molar ratio is stoichiometric as, in the event of a large defect of hydrochloric acid, quinapril tends to cyclise to form the diketopiperazine shown above, while in the event of an excess of acid, decomposition of the quinapril hydrochloride, and of the benzyl ester of quinapril itself, takes place.

Generally, hydrochloric acid is added at room temperature, and the reaction between the hydrochloric acid and the benzyl ester of quinapril (II) is virtually immediate, within minutes.

Because the solution of the benzyl ester of quinapril hydrochloride in isopropanol is more stable than the solution of the free base and, on the other hand, considering the instability of the benzyl ester of quinapril (II), the most reliable manner of preserving such product for short periods of time is maintaining it as the hydrochloride in solution in isopropanol.

Once hydrogenation is finalised, the catalyst is removed, for example, by filtration, and the solvent employed, ethanol or isopropanol, is removed, for instance, by vacuum distillation, at a temperature below 40° C., as at greater temperatures cyclisation of the product to form the diketopiperazine is quantitatively more significant, and toluene is added. These operations involving the removal of the solvent and addition of toluene can be repeated a variable number of times. Subsequently, the bulk of the reaction is allowed to stand at room temperature for the quinapril hydrochloride to precipitate in the form of the toluene solvate.

In a specific embodiment, for the obtaining of the toluene solvate of quinapril hydrochloride starting from the raw solution in the solvent used (ethanol or isopropanol), said solution is distilled down to a defined volume of approximately 1,6 ml/g of benzyl ester of quinapril and subsequently, an amount of toluene of approximately 2,25 ml of toluene per gram of benzyl ester of quinapril is added. After this, distillation is carried out again to the same volume as before, and the same amount of toluene is added. By working under these conditions, quinapril hydrochloride precipitates in the form of the toluene solvate within a period of time comprised between 20 and 60 minutes. By following this precipitation process for this toluene solvate, using isopropanol as a solvent, a greater yield is obtained than by employing ethanol, which can largely be accounted for by the fact that quinapril hydrochloride is more soluble in ethanol than in isopropanol.

The toluene solvate of precipitated quinapril hydrochloride is filtered and dried, and a yield comprised between approximately 85% and 90% is obtained. This solvate is a very suitable intermediate for the subsequent purification of quinapril hydrochloride according to the process proposed by the present invention. The spectroscopic characteristics (IR, $^1$H-NMR and $^{13}$C-NMR) of this toluene solvate are contained in Example 2.1. The attempts made to remove the toluene by drying of said solvate, without degrading the quinapril hydrochloride, were unsuccessful.

Subsequently, the toluene solvate of quinapril hydrochloride is treated with a solvent belonging to Class 3, i.e., non-toxic, non-carcinogenic, for example, ethyl formate or methyl acetate, at a temperature comprised between 40° C. and 45° C., for a period of time comprised between 1 and 2 hours, and it is next cooled down to a temperature comprised between 20° C. and 25° C., for a period of time comprised between 1 and 2 hours, to form the corresponding solvate, either of ethyl formate or of methyl acetate, which is then filtered and dried, with a yield in any of the cases of approximately 95%. These solvates can be dried in an oven, to remove the solvent, without degrading the quinapril hydrochloride. These solvates are key intermediates for obtaining quinapril hydrochloride of a high degree of purity (99.8%) according to the process object of this invention. The spectroscopic (IR, $^1$H-NMR and $^{13}$C-NMR) and X-Ray difraction characteristics of these solvates are contained in Examples 2.2 and 2.3.

The drying of the ethyl formate or of the methyl acetate solvates of quinapril hydrochloride obtained in this manner, in order to yield quinapril hydrochloride, can be carried out in an oven, for example in a vacuum oven, at a temperature comprised between approximately 40 and 50° C., for a period of time comprised between 12 and 24 hours, depending on the amount of solvate to be dried. The resulting quinapril hydrochloride, the spectroscopic (IR, $^1$H-NMR and $^{13}$C-NMR), optical rotation and X-Ray diffraction characteristics of which are collected in example 2.4., is an amorphous product, the X-ray diffraction patter of which exhibits few peaks and with a low intensity, and consequently, a priori, it is an amorphous product.

The hydrogenation of the product resulting after the addition of hydrochloric acid or of the solution of hydrogen chloride in isopropanol in step a) can be carried out without prior isolation of the intermediate formed. Equally, the bulk of the reaction resulting from the hydrogenolysis can be subjected to distillation in order to remove the solvent used in step a), without isolation of the product formed.

In a specific and preferred embodiment of the invention, the benzyl ester of quinapril is obtained by condensation of the N-carboxyanhydride of N-[1-(S)-ethoxycarbonyl-3-phenylpropyl]-L-alanine and of the benzyl ester of (S)-1,2,3,4-tetrahydro-3-isoquinolinecarboxylic acid. The resulting benzyl ester of quinapril (II), without isolating, is subjected to the previously described treatment, for example, in patent BE 892.552.

The following examples serve the purpose of illustrating specific forms of embodiment of the process object of the invention, and they must not be considered as limiting to the scope of the same. All the X-ray diffraction analyses were carried out by the crystalline powder method (λ=1,5419 Å), the preparations of the sample were performed on a dry standard.

Material of the anode: copper

Wavelength, $\lambda_1$ (Å)=1,54060

Wavelength, $\lambda_2$ (Å)=1,54439

Initial angle (2θ°): 6,025

Final angle (2θ°): 39,9855

Initial d value (Å)=14,65735

Final d value (Å)=2,25302

EXAMPLE 1

Preparation of the Benzyl Ester of (S,S,S) 2-[2-[(1-(Ethoxycarbonyl)-3-phenylpropyl)amino]1-oxopropyl]-1,2,3,4-tetrahydro-3-isoquinolinecarboxylic Acid [Benzyl Ester of Quinapril (II)]

51.3 g (0.12 moles) of the para-toluenesulfonate of the benzyl ester of (S)-1,2,3,4-tetrahydro-isoquinoline-3-carboxylic acid are suspended in 150 ml of toluene. 200 ml of 10% sodium bicarbonate solution are added under stirring and the mixture is shaken until complete dissolution is achieved. The organic phase is allowed to decant and it is separated, and the same is again washed with 100 ml of 10% sodium bicarbonate solution, and it is subsequently dried with sodium sulphate and filtered. To this toluene based solution, 36.0 g (0.12 moles) of the N-carboxyanhydride of N-[1-(S)-ethoxycarbonyl-3-phenylpropyl]-L-alanine, dissolved in 75 ml of toluene, are added, at room temperature, in 1 hour. Approximately 4 hours after the addition of said N-carboxyanhydride, the reaction is finished. The toluene phase is washed with a 5% sodium hydroxide solution, followed by water, and the solvent is vacuum-distilled until an oil is obtained, 62 g (Yield: 98%) which is the benzyl ester of quinapril.

After forming the maleate, it is characterized by:

HPLC: the has a purity of 99.3%

Titration: 100.2%

$[\alpha]^R$=12.93 (2% methaol) IR (KBr) (ν, cm$^{-1}$):3520, 3050, 2980, 1746, 1656, 1603, 1455, 1347, 1211, 1010, 751, 697.

In a solution, this compound is a mixture of two rotamers. The distribution of the rotamers is observed, in some cases, in the proton and carbon 13 nuclear magnetic resonance (NMR) spectra.

$^1$H-NMR ($CDCl_3$, 300 MHz) (δ (ppm)): 10,40 (wide band, 3H); 7,40–7,00 (m, 14H); 6,29 (s, 2H); 5,43 (dd, $J_1$=3,9 Hz, $J_2$=5,9 Hz, 1H); 5,02 (m, 2H); 4,60 (m, 2H); 4,44 (q, $J_1$=$J_2$=$J_3$=7,1 Hz, 1H); 4,23 (m, 2H); 3,77 ($t_{min}$), 3,72 (t, $J_1$=6,3 Hz, 1H); 3,45–3,05 (m, 2H); 2,85–2,65 (m, 2H); 2,30–2,15 (m, 2H); 1,6 ($d_{min}$, $J_1$=6,8 Hz), 1,45 (d, $J_1$=6,9 Hz), 3H; 1,28 (t, $J_1$=$J_2$=7,2 Hz, 3H). $^{13}$C-NMR ($CDCl_3$, 75 MHz) (δ (ppm)): 170,4 (min), 170,1, 169,7 (min), 169,2 (min), 169.1, 139,6 (min), 139,5, 135,3, 135,1 (min), 134,5, 131,8, 131,3 (min), 130,9 (min), 130,7, 128,6, 128,5, 128,4, 128,3, 128,1, 128,0, 127,9, 127,8, 127,7, 127,4, 127,3, 126,6, 126,5, 126,4 126,1, 67,9 (min), 67,2, 62,6, 62,4 (min), 59,5 (min, 58,6, 54,7 (min), 54,5 (min), 53,5, 52,6, 45,2, 44,5 (min), 32,4 (min), 32,1, 31,3 (min), 31,2, 30,5, 16,8 (min), 15,6, 14,0 (min), 13,9.

EXAMPLE 2

Preparation of (S,S,S) 2-[2-[(Ethoxycarbonyl)-3-phenylpropyl)amino]1-oxopropyl]-1,2,3,4-tetrahydroisoquinoline-3-carboxylic Acid Hydrochloride [Quinapril Hydrochloride (I)]

2.1. Toluene Solvate of Quinapril Hydrochloride.

62.0 g of the benzyl ester of quinapril, obtained according to Example 1, are dissolved with 400 ml of ethanol and 10 ml of concentrated hydrochloric acid, 3.1 g of 5% Pd/C (paste) catalyst are added and the mixture is hydrogenated at room temperature and at a pressure $10^5$ Pa (1 bar) for 3 hours. After hydrogenation has concluded, the catalyst is filtered, most part of the ethanol is vacuum-distilled and 150 ml of toluene are added. Subsequently, most of the solvent is vacuum-distilled again and another 150 ml of toluene are added. Subsequently it is allowed to stand at room temperature, which leads to the precipitation of a solid which is filtered and dried under a vacuum at 40° C. 58,5 g were obtained (Yield: 88%) of a product which corresponds to the toluene solvate of quinapril hydrochloride.

IR (KBr) (ν, $cm^{-1}$): 3520, 3026, 3003, 2928, 2802, 1755, 1742, 1711, 1646, 1558, 1538, 1495, 1455, 1203, 758, 737.

In solution, this compound is a mixture of two rotamers. The distribution of the rotamers is observed, in some cases, in the proton and carbon 13 nuclear magnetic resonance (NMR) spectra.

$^1$H-NMR ($CDCl_3$, 300 MHz) (δ (ppm)): 7,20–7,00 (m, 14H); 5,15 (t wide), 4,97 ($width_{min}$), 1H; 4,82–4,45 (m, 3H); 4,35–4,05 (m, 2H), 3,90 (t wide, 1H); 3,42–3,05 (m, 2H), 2,90–2,62 (m, 2H), 2,42–2,20 (m, 2H), 2,38 (s, 3H), 1,68 (d, $J_1$=6,2 Hz); 1,60 ($d_{min}$, $J_1$=6,2 Hz), 3H; 1,28 ($t_{min}$, $J_1$=$J_2$=4,0 Hz); 1,22 (t, $J_1$=$J_2$=4.0 Hz), 3H; $^{13}$C-NMR ($CDCl_3$, 75 MHZ) (δ (ppm)): 172,2, 171,4 (min) 169,2, 168,6, 168,2 (min), 168,0 139,6 (min), 139,4, 137,8, 132,2, 131,4, 131,3, 131,2, 129,0, 128,6, 128,4, 128,2, 127,7, 127,1, 126,4, 126,3, 126,2, 125,2, 63,2 (min), 62,9, 59,1 (min), 58.9, 54,9 (min), 54,6 (min), 54,5, 53,1, 45,4, 44,1 (min), 31,9 (min), 31,4, 31,1, 31,0, 30,1 (min), 21,4, 16,2 (min), 15,2, 14,0 (min), 13,9.

2.2. Ethyl Formate Solvate of Quinapril Hydrochloride.

The 58.5 g of toluene solvate are shaken at 40–45° C. with 234 ml of ethyl formate, for 2 hours, and is subsequently cooled down to a temperature comprised between 20 and 25° C. for two additional hours. The resulting product is filtered and dried in a vacuum oven at a temperature of 30° C., for four hours, to obtain 54 g of ethyl formate solvate of quinapril hydrochloride (Yield: 95%).

IR (KBr) (ν, $cm^{-1}$): 3520, 3028, 3001, 2979, 2935, 2857, 1744, 1718, 1648, 1546, 1495, 1462, 1454, 1432, 1388, 1260, 1199, 756.

In solution, this compound is a mixture of two rotamers. The distribution of the rotamers is observed, in some cases, in the proton and carbon 13 nuclear magnetic resonance (NMR) spectra.

$^1$H-NMR ($CDCl_3$, 300 MHz) δ (ppm)): 10,00 (s wide, 1H), 8,95 (s wide, 1H), 8,02 (s, 1H); 7,15 (m, 9H); 5,15 ($J_1$=$J_2$=5,6 Hz), 4,95 ($width_{min}$), 1H; 4,82–4,62 (m, 2H); 4,60–4,42 (m, 1H); 4,20 (q, ($J_1$=$J_2$=$J_3$=7,0 Hz, 2H); 4,09–3,90 (m, 1H); 3,68 ($q_{min}$); 3,40–3,05 (m, 2H), 2,97–2,59 (m, 2H); 2,42–2,20 (m, 2H); 1,67 (d, $J_1$=7,0 Hz), 1,56 ($d_{min}$, $J_1$=7,0 Hz, 1H), 1,30 (t, $J_1$=$J_2$=7,0 Hz), 1,18 ($J_1$=$J_2$=7,0 Hz), 3H. $^{13}$C-NMR ($CDCl_3$, 75 MHz) (δ (ppm)): 172,2, 171,3 (min), 169,2 (min), 168,6, 168,0, 161,0, 139,7 (min), 139,4, 132,2, 131,4 (min), 131,3 (min), 131,2, 128,5 (min), 128,4, 128,2, 127,2, 127,1, 126,3, 126,2, 126,1, 63,1 (min), 62,9, 59,9, 59,1 (min), 58,9, 58,2 (min), 54,8 (min), 54,6 (min), 54,5, 53,1, 45,4, 44,1 (min), 31,8 (min), 31,3, 31,1, 31,0, 30,8 (min), 30,1, 16,2 (min), 15,2, 14,1, 14,0 (min), 13,9.

X-Ray Diffraction (powder)
Ethyl formate solvate of quinapril hydrochloride

| Angle (2θ°) | Relative intensity (%) |
|---|---|
| 8.82 | 32.7 |
| 10.88 | 23.3 |

-continued

X-Ray Diffraction (powder)
Ethyl formate solvate of quinapril hydrochloride

| Angle (2θ°) | Relative intensity (%) |
|---|---|
| 11.47 | 20.9 |
| 12.05 | 16.5 |
| 13.63 | 34.4 |
| 15.89 | 12.5 |
| 16.08 | 17.2 |
| 16.48 | 27.4 |
| 16.85 | 32.7 |
| 18.05 | 10.4 |
| 18.42 | 17.8 |
| 18.68 | 24.6 |
| 19.52 | 50.7 |
| 19.75 | 33.2 |
| 20.11 | 45.3 |
| 21.20 | 36.6 |
| 21.86 | 100.0 |
| 23.07 | 15.3 |
| 23.59 | 30.1 |
| 24.50 | 42.5 |
| 26.66 | 14.5 |
| 27.16 | 22.7 |
| 27.45 | 10.6 |
| 28.34 | 13.1 |
| 28.71 | 15.6 |
| 29.66 | 29.5 |
| 30.56 | 14.5 |
| 34.87 | 13.5 |

2.3. Methyl Acetate Solvate of Quinapril Hydrochloride

Following a similar process to that described in Example 2.2., but changing ethyl formate for methyl acetate, the corresponding methyl acetate solvate of quinapril hydrochloride (Yield: 95%) was obtained, which is characterised by the following spectroscopic data.

IR (KBr) (ν, $cm^{-1}$): 3500, 3084, 3003, 2860, 1746, 1735, 1706, 1648, 1545, 1495, 1455, 1259, 1196, 755.

In solution, this compound is a mixture of two rotamers. The distribution of the rotamers is observed, in some cases, in the proton and carbon 13 nuclear magnetic resonance (NMR) spectra. $^1$H-NMR ($CDCl_3$, 300 MHz) (δ (ppm)): 10,10 (s wide, 1H); 9,10 (s wide, 1H); 7,21–7,06 (m, 9H); 5,14 (t, $J_1$=$J_2$=5,6 Hz, 1H); 4,80–4,67 (m, 2H); 4,57 (m, 1H); 4,21–4,19 (m, 2H); 4,16–3,89 (m, 1H); 3,66 (s, 3H), 3,41–3,00 (m, 2H); 2,72–2,62 (m, 2H); 2,34–2,29 (m, 2H); 2,05 (s, 3H); 1,67 (d, $J_1$=6,8 Hz), 1,57 ($d_{min}$, $J_1$=6,8 Hz), 3H; 1,21 ($t_{min}$, $J_1$=$J_2$=6,9 Hz); 1,17 (t, $J_1$=$J_2$=6,9 Hz), 3H. $^{13}$C-NMR ($CDCl_3$, 75 MHz) (δ (ppm)): 172,2 171,5 (min), 169,2 (min), 168,6, 168,3 (min), 168,1, 139,6 (min), 139,4, 132,2, 131,5 (min), 131,3 (min), 131,2, 128,6, 128,4, 128,3 (min), 127,8 (min), 127,2, 126,4, 126,2 (min), 63,2 (min), 62,9, 58,9, 54,7 (min), 54,5, 53,2, 51,5, 45,4, 44,2 (min), 31,9 (min), 31,4, 31,1, 31,0, 30,2, 20,6, 16,1 (min), 15,5, 14,0 (min), 13.9.

X-Ray Diffraction (powder)
Methyl acetate solvate of quinapril hydrochloride

| Angle (2θ°) | Relative intensity (%) |
|---|---|
| 8.86 | 26.0 |
| 10.95 | 26.0 |
| 11.79 | 19.2 |
| 13.73 | 45.9 |
| 16.18 | 18.2 |
| 16.57 | 37.7 |

-continued

| X-Ray Diffraction (powder) Methyl acetate solvate of quinapril hydrochloride | |
|---|---|
| Angle (2θ°) | Relative intensity (%) |
| 16.87 | 60.4 |
| 18.76 | 18.6 |
| 18.93 | 18.6 |
| 19.59 | 33.2 |
| 20.16 | 81.9 |
| 20.91 | 19.2 |
| 21.56 | 30.7 |
| 21.93 | 100.0 |
| 22.18 | 28.7 |
| 23.22 | 14.6 |
| 23.65 | 35.4 |
| 24.62 | 52.6 |
| 27.17 | 34.0 |
| 28.51 | 16.6 |
| 28.93 | 22.9 |
| 30.69 | 21.6 |
| 30.85 | 14.0 |

2.4. Quinapril Hydrochloride

The ethyl formate or methyl acetate solvates of quinapril hydrochloride, obtained according to Examples 2.2. and 2.3., can be dried directly in a vacuum oven at a temperature comprised between 40 and 50° C. for a period of time comprised between 12 and 14 hours, without the need of isolating them, in order to give the quinapril hydrochloride, which is a very scarcely crystalline or an amorphous product, as evidenced by its X-ray diffraction pattern. Out of the 54 g of ethyl formate solvate of quinapril hydrochloride 46 g of quinapril hydrochloride are obtained, characterised by:

HPLC: 99.8%

Titration: 100.2%

$[\alpha]^R$=+15.9° (2% methanol)

IR (KBr) (ν, $cm^{-}$): 3415, 3059, 2982, 2936, 1740, 1651, 1541, 1497, 1473, 1455, 1443, 1386, 1379, 1207, 751, 702.

In solution, quinapril hydrochloride is a mixture of two rotamers. The distribution of the rotamers is observed, in some cases, in the proton and carbon 13 nuclear magnetic resonance (NMR) spectra.

$^1$H-NMR ($CDCl_3$, 300 MHz) (δ (ppm)): 7,23 (m, 9H); 5,12 (m, 1H), 4,9–4,4 (m, 3H); 4,19 (m, 2H); 3,91 (m); 3.79 ($m_{min}$), 1H; 3,3–3,1 (m, 2H); 2,77–2,61 (m, 2H); 2,20 (m, 2H); 1,51 (d, $J_1$=6,4 Hz), 1,49 ($d_{min}$, $J_1$=5,1 Hz), 3H; 1,22 ($t_{min}$, $J_1$=$J_2$=7,3 Hz), 1,17 (t, , $J_1$=$J_2$=7,3 Hz), 3H. $^{13}$C-NMR ($CDCl_3$, 75 MHz) (δ (ppm)): 171,5, 171,4, 168,5, 140,2, 132,5, 132,4, 132,1 (min), 131,5 (min), 128,5, 128,4, 128,2, 128,1, 127,1, 126,7, 126,6, 126,3, 126,1, 125,4, 62,2 (min), 62,0, 57,4 (min), 57,3, 53,9 (min), 53,1 (min), 52,7, 52,0, 44,5, 43,6 (min), 31,3 (min), 30,8, 30,6 (min), 30,4, 30,0, 21,1 (min), 16,2 (min), 14,7, 13,9.

| X-Ray Diffraction (powder) Quinapril hydrochloride | |
|---|---|
| Angle (2θ°) | Relative intensity (%) |
| 11.18 | 31.9 |
| 12.17 | 29.4 |
| 17.38 | 33.9 |
| 19.83 | 37.9 |
| 28.34 | 10.0 |

What is claimed is:

1. A process for obtaining quinapril hydrochloride of formula (I)

(I)

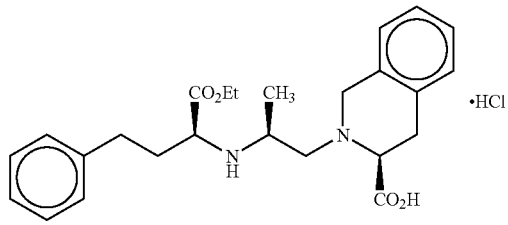

which comprises the stages of:

a) treatment of the benzyl ester of quinapril (II)

(II)

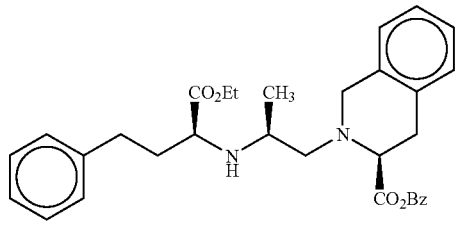

where Bz is the benzyl radical, with alcohol and hydrochloric acid or hydrogen chloride and hydrogenation of same through the addition of an appropriate hydrogenation catalyst;

b) removal of the solvent used in step a);

c) addition of toluene to precipitate the quinapril hydrochloride as a toluene solvate;

d) treatment of the toluene solvate of quinapril hydrochloride with a solvent belonging to class 3, capable of forming a solvate of quinapril hydrochloride from which it is possible to eliminate said solvent by drying in an oven without degrading the quinapril hydrochloride; and e) drying of the solvate obtained in step d) at a temperature between 40° C. and 50° C. to yield quinapril hydrochloride (I).

2. A process according to claim 1 wherein the hydrogenolysis reaction of the benzyl ester of quinapril (II) is carried out in a alcoholic solvent, with treatment with concentrated hydrochloric acid or with a solution of hydrogen chloride in isopropanol, and hydrogenation with hydrogen gas in the presence of a hydrogenation catalyst.

3. A process according to claim 2, wherein said alcoholic solvent is [chosen from between] *either* ethanol or isopropanol.

4. A process according to claim 2, wherein the hydrogenation is carried out at a pressure [comprised] *in the range of* $10^4$ Pa and $2\times10^5$ Pa.

5. A process according to claim 2, wherein the hydrogenation is carried out at a temperature [comprised] *in the range of* 10 and 40° C.

6. A process according to claim 2, wherein the hydrogenation catalyst is Pd/C.

7. A process according to claim 2, wherein the hydrogenolysis reaction of the benzyl ester of quinapril (II) is carried out using ethanol as a solvent, concentrated hydrochloric acid, *at* a pressure of $1\times10^5$ Pa (1 bar) and *at* room temperature.

8. The process according to claim 2, wherein the hydrogenolysis reaction of the benzyl ester of quinapril (II) is carried out using isopropanol as a solvent, a solution of hydrogen chloride in isopropanol, a pressure of $2\times10^5$ Pa (1 bar) and a temperature of approximately 30° C.

9. A process according to claim 2 wherein the molar ratio between the benzyl ester of quinapril (II) and the hydrochloric acid can be equal or greater in a proportion of 1.1 (benzyl ester of quinapril (II)) to 1 (hydrochloric acid) with respect to stoichiometric one.

10. A process according to claim 1, wherein the removal of the solvent used in stage a) is carried out by vacuum-distillation.

11. A process according to claim 1, wherein the Class 3 solvent used to treat the toluene solvate of quinapril hydrochloride is chosen from among ethyl formate and methyl acetate.

12. A process according to claim 1, wherein the treatment of the toluene solvate of quinapril hydrochloride with the class 3 solvent is carried out at a temperature [comprised] between 40° C. and 45° C., for a period of time [comprised] between 1 and 2 hours, and is subsequently cooled down to a temperature [comprised] between 20° C. and 25° C. for a period of time [comprised] between 1 and 2 hours.

13. A process according to claim 1, wherein the Class 3 solvent solvate of quinapril hydrochloride is chosen from among ethyl formate solvate of quinapril hydrochloride and the methyl acetate solvate of quinapril hydrochloride.

14. A process according to claim 1, wherein the Class 3 solvent solvate of quinapril hydrochloride is dried in a vacuum oven, at a temperature [comprised] between 40 and 50° C. for a period of time [comprised] between 12 and 24 hours.

*15. A process according to claim 1, wherein the hydrogenation of the product resulting after the addition of hydrochloric acid or hydrogen chloride to the benzyl ester of quinapril (II) in stage a), is carried out without prior isolation of the intermediate formed.*

*16. A process according to claim 1, wherein the benzyl ester of quinapril (II) is obtained by condensation of the N-carboxyanhydride of N-[1-(S)-ethoxycarbonyl-3-phenylpropyl]-L-alanine and of the benzyl ester of (S)1,2,3,4-tetrahydro-3-isoquinolinecarboxylic acid, followed by hydrogenation in an acid medium.*

*17. A process according to claim 16, wherein the benzyl ester of quinapril (II) obtained is used without prior isolation.*

*18. A toluene solvate of quinapril hydrochloride characterized in that its infrared spectrum presents the following peaks:*

*IR (KBr) (ν, $cm^{-1}$) 3520, 3026, 3003, 2928, 2802, 1755, 1742, 1711, 1646, 1558, 1538, 1495, 1455, 1203, 758, 737.*

*19. An ethyl formate solvate of quinapril hydrochloride characterized in that its x-ray diffraction pattern presents the following characteristics:*

| X-Ray Diffraction (powder) Ethyl formate solvate of quinapril hydrochloride | |
|---|---|
| Angle (2θ°) | Relative Intensity (%) |
| 8.82 | 32.7 |
| 10.88 | 23.3 |
| 11.47 | 20.9 |

-continued

| X-Ray Diffraction (powder) Ethyl formate solvate of quinapril hydrochloride | |
|---|---|
| Angle (2θ°) | Relative Intensity (%) |
| 12.05 | 16.5 |
| 13.63 | 34.4 |
| 15.89 | 12.5 |
| 16.08 | 17.2 |
| 16.48 | 27.4 |
| 16.85 | 32.7 |
| 18.05 | 10.4 |
| 18.42 | 17.8 |
| 18.68 | 24.6 |
| 19.52 | 50.7 |
| 19.75 | 33.2 |
| 20.11 | 45.3 |
| 21.20 | 36.6 |
| 21.86 | 100.0 |
| 23.07 | 15.3 |
| 23.59 | 30.1 |
| 24.50 | 42.5 |
| 26.66 | 14.5 |
| 27.16 | 22.7 |
| 27.45 | 10.6 |
| 28.34 | 13.1 |
| 28.71 | 15.6 |
| 29.66 | 29.5 |
| 30.56 | 14.5 |
| 34.87 | 13.5. |

*20. An ethyl formate solvate of quinapril hydrochloride according to claim 19, characterized in that its infrared spectrum presents the following peaks:*

*IR (KBr) (ν, $cm^{-1}$): 3520, 3028, 3001, 2979, 2935, 2857, 1744, 1718, 1648, 1546, 1495, 1462, 1454, 1432, 1388, 1260, 1199, 756.*

*21. A methyl acetate solvate of quinapril hydrochloride characterized in that its x-ray diffraction pattern presents the following characteristics:*

| X-Ray Diffraction (powder) Methyl acetate solvate of quinapril hydrochloride | |
|---|---|
| Angle (2θ°) | Relative intensity (%) |
| 8.86 | 26.0 |
| 10.95 | 26.0 |
| 11.79 | 19.2 |
| 13.73 | 45.9 |
| 16.18 | 18.2 |
| 16.57 | 37.7 |
| 16.87 | 60.4 |
| 18.76 | 18.6 |
| 18.93 | 18.6 |
| 19.59 | 33.2 |
| 20.16 | 81.9 |
| 20.91 | 19.2 |
| 21.56 | 30.7 |
| 21.93 | 100.0 |
| 22.18 | 28.7 |
| 23.22 | 14.6 |
| 23.65 | 35.4 |
| 24.62 | 52.6 |
| 27.17 | 34.0 |
| 28.51 | 16.6 |
| 28.93 | 22.9 |
| 30.69 | 21.6 |
| 30.85 | 14.0. |

*22. A methyl acetate solvate of quinapril hydrochloride according to claim 21, characterized in that its infrared spectrum presents the following peaks:*

*IR (KBr) (ν, $cm^{-1}$) 3500, 3084, 3003, 2860, 1746, 1735, 1706, 1648, 1545, 1495, 1455, 1259, 1196, 755.*

*23. A solvate of quinapril hydrochloride, wherein said solvate is formed using a Class 3 solvent.*

*24. The solvate of quinapril hydrochloride according to claim 23, wherein said Class 3 solvent is selected from the group consisting of ethyl formate and methyl acetate.*

*25. A solvate of quinapril hydrochloride, said solvate obtained by*

*a) treating a benzyl ester of quinapril having the following structure:*

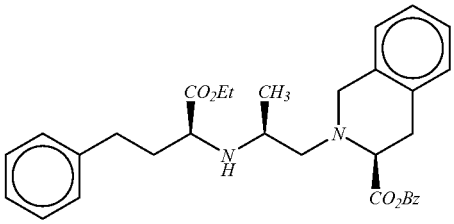

*where Bz is the benzyl group, with a solvent of alcohol and hydrochloride acid or hydrogen chloride and hydrogenating through the addition of an appropriate hydrogenation catalyst;*

*b) removing the solvent used in step a);*

*c) adding toluene to precipitate the quinapril hydrochloride as a toluene solvate; and*

*d) treating the toluene solvate of quinapril hydrochloride with a solvent belonging to Class 3, capable of forming a solvate of quinapril hydrochloride from which it is possible to eliminate said solvent by drying in an oven without degrading the quinapril hydrochloride.*

*26. A toluene solvate of quinapril hydrochloride.*

*27. A toluene solvate according to claim 26, wherein said toluene solvate is obtained by*

*a) treating a benzyl ester of quinapril having the following structure:*

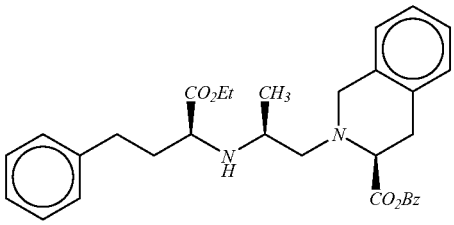

*where Bz is the benzyl group, with a solvent of alcohol and hydrochloric acid or hydrogen chloride and hydrogenating through the addition of an appropriate hydrogenation catalyst;*

*b) removing the solvent used in step a);*

*c) adding toluene to precipitate the quinapril hydrochloride as a toluene solvate.*

*28. A process of producing quinapril hydrochloride, said process comprising forming a solvate of quinapril hydrochloride using a Class 3 solvent.*

*29. The process according to claim 28, wherein the Class 3 solvent is selected from the group consisting of ethyl formate and methyl acetate.*

* * * * *